US006976841B1

(12) United States Patent
Osterwalder

(10) Patent No.: US 6,976,841 B1
(45) Date of Patent: Dec. 20, 2005

(54) INTRA ORAL DENTAL IRRADIATION DEVICE FOR MATERIAL CURING AND DENTAL IMAGING

(75) Inventor: J. Martin Osterwalder, Cardiff, CA (US)

(73) Assignee: Nova Ranger, Inc., San Diego, CA (US)

( * ) Notice: Subject to any disclaimer, the term of this patent is extended or adjusted under 35 U.S.C. 154(b) by 76 days.

(21) Appl. No.: 10/324,776

(22) Filed: Feb. 12, 2003

Related U.S. Application Data

(60) Provisional application No. 60/358,636, filed on Feb. 21, 2002.

(51) Int. Cl.$^7$ ............................................... A61C 1/00
(52) U.S. Cl. ..................................................... 433/29
(58) Field of Search .......................... 433/29; 600/237, 600/241

(56) References Cited

U.S. PATENT DOCUMENTS

| | | | |
|---|---|---|---|
| 4,324,546 A * | 4/1982 | Heitlinger et al. ............. | 433/25 |
| 4,447,209 A | 5/1984 | Sutter .......................... | 433/173 |
| 5,316,473 A | 5/1994 | Hare | |
| 5,487,662 A * | 1/1996 | Kipke et al. .................. | 433/37 |
| 5,995,583 A | 11/1999 | Schick et al. | |
| 6,077,073 A | 6/2000 | Jacob | |
| 6,102,696 A | 8/2000 | Osterwalder et al. .......... | 433/29 |
| 6,162,055 A * | 12/2000 | Montgomery et al. ....... | 433/216 |
| 6,611,110 B1 * | 8/2003 | Fregoso ....................... | 315/224 |
| 6,616,447 B1 * | 9/2003 | Rizoiu et al. ................. | 433/29 |
| 2003/0148243 A1 * | 8/2003 | Kerschbaumer et al. ...... | 433/29 |

OTHER PUBLICATIONS

U.S. Appl. No. 60/327,908.*

* cited by examiner

Primary Examiner—Cary E. O'Connor
(74) Attorney, Agent, or Firm—Donn K. Harms

(57) ABSTRACT

An intra-oral dental irradiation device for use in dental procedures for whitening teeth, imaging teeth, and making impressions of tooth structures of a patient. The device features one or a plurality of LED devices mounted to an arched shaped structure which project light upon or through teeth. In the whitening mode the light of the proper spectrum to activate enamel whitening material is projected. In the imaging mode light projected by the LED devices is received by a charged coupled device which communicates the image of the light passing through the teeth from the LED devices, to a computer. In making dental impressions, the device projects light in a spectrum that provides the catalyst to material that hardens when exposed to that spectrum thereby hardening dental impression material when inserted over the teeth of a patient.

27 Claims, 2 Drawing Sheets

INTRA ORAL DENTAL IRRADIATION DEVICE FOR MATERIAL CURING AND DENTAL IMAGING

FIELD OF THE INVENTION

This application claims the benefit of U.S. Provisional application Ser. No. 60/358,636 filed on Feb. 21, 2002. This invention relates to a device for providing irradiated energy at low voltage inside the mouth. More particularly this invention relates to a device that provides light energy inside the mouth at determined wavelengths which will provide for the imaging and display in real time of the internal structure of teeth by using visible light projected through the teeth to sensors sensitive to the particular wavelength of light so projected. Additionally, the device when emitting light energy at specific wavelengths can be used for the activation and resulting curing of liquid and semi-liquid materials, used in commercial dental applications. Such materials are widely used in dentistry for forming dental impressions, teeth whitening, filling cavities, and similar tasks. Materials used for such purposes are cured or hardened to a desired level when subjected to irradiation with photons of proper predetermined wavelength.

BACKGROUND OF THE INFORMATION

Dental imaging of internal tooth structure is conventionally accomplished by using a source of soft x-rays projected through the teeth of a patient. Also using projection of light in the visible spectrum are dental procedures for whitening teeth as well as hardening material to make dental impressions.

The x-ray projection device generally is large and cumbersome and projected externally to the head of a patient through a determined position on the patient's jaw. Sensitive film material is placed behind a tooth or series of teeth at the desired location, thereby forming a shadow image on the film from the x-rays which penetrate through the teeth from the projection device.

Thereafter, the exposed film then needs to be developed, using chemical or other processes before the results can be viewed by the dentist. This procedure exposes both the x-ray technician and the patient to irradiated x-rays and is slowed by the need to develop the film.

Newer technology makes use of charge coupled devices (CCDs) instead of film material. Such devices receive the x-rays transmitted through the teeth from the projection device and allow for the digitizing of the tooth pictures allowing for immediate display and imaging of the results on a monitor after x-ray exposure. This technique, while faster, also causes the patient and the technician to be exposed to X-ray radiation at other unwanted parts of the body, which may be dangerous.

Dental impressions are still commonly handled by making negative castings of a section or all of the dental arch. Conventionally, casting material made from kelp or other material which hardens using a catalyst is used for making the negative impression of the teeth. Generally the casting material is mixed with a catalyst and then used to fill a dental tray selected to fit the patient's mouth dimensions. The selected tray, filled with the impression material, is then placed in the mouth wherein the patient sinks his teeth into the material down to the gum line. After about 3–5 minutes the impression material is removed from the teeth and a negative impression is formed therein from which a positive model of the teeth can be obtained using other molding material. The catalyst for the impression material can either be chemical or just as in the case of dental surface whitening, it may be light activated.

The herein described apparatus and method provide for the projection of energy at determined wavelengths to the task in the visible and invisible spectrum at low energy with great specificity as to location. This removes, or at least considerably diminishes, the radiation hazard to the patient and technician and makes real-time imaging of internal teeth structures possible. In addition to imaging, the described apparatus can also provide additional functions common to modern dentistry through the provision of projected light at wavelengths that cure impression material and/or tooth filling material and/or activate teeth whitening compounds.

There are many liquid and semi-liquid materials which can be activated by irradiation with high-energy photons. The incident radiation at a determined wavelength initiates an intended chemical chain reaction in these materials or compounds causing them to cure or harden. Such materials are also conventionally used for commercial applications such as light activated curing of sealants for parts assemblies.

In dentistry such photon induced curing of compounds is commonly used for filling cavity and repair of tooth chips and external tooth surfaces and the like. The same curing technique is also used for making dental impressions of a patient's mouth and tooth structure and is also used to activate teeth whitening substances such as hydrogen peroxide compounds containing photon sensitive accelerator materials.

Conventional photon sources for such curing processes are emitting in the visible or UV portion of the energy spectrum. While early photon sources made use of halogen tubes and bulky, high voltage gas lasers, newer devices make use of light emitting diodes (LED), and diode lasers. These latter devices allow for the design of a more compact, low voltage curing apparatus and one which has better efficiency in converting input power to light output power. The wavelength required in such curing and whitening equipment and procedures is dictated by the material used and that compound's spectral absorption characteristics, which generally tend to be rather specific.

U.S. Pat. No. 6,102,696 (Osterwalder) teaches a self contained light source for curing light initiated resins used to coat teeth as veneers and fill cavities and chips in teeth in aesthetic or restorative procedures. Osterwalder, while providing a great leap forward in utility and convenience in the curing of such dental material, is intended for curing in small specific areas and not intended to provide imaging.

U.S. Pat. No. 6,077,073 (Jacob) relates to an elongated sheathed light emitting diode array apparatus which is also specifically designed for curing resins in dentistry for localized fillings in cavities. Jacob too lacks registration of the projected photons to an imaging device and would not be suitable for such applications as imaging. Nor would Jabob be suitable for curing of impressions and activating whitening agents, which are discussed herein. Such applications require an apparatus designed to form images from a specific projection point on a specific registered reception point and also to activate and cure compounds which are spread over large areas and are applied in thicker layers than those applied for cavity filling purposes.

U.S. Pat. No. 5,316,473 (Hare) teaches a device for light curing of a large area in the mouth. However, Hare teaches the use of either fiber optics or LEDs which are not powerful enough nor very efficiently directed towards the desired areas. Hare thus suffers from the same drawback of ineffective application of the curing light source and of insufficient power density for curing/whitening of thick layers of compounds. Furthermore, this apparatus is of rigid design and requires the fabrication of several different models of trays to accommodate all possible dental shapes.

As such, there is a need for further improvements of the state of the art in creating novel dental imaging and curing equipment. Such a device should be flexible and require low voltage while still being capable of irradiating large areas of the dental arch for impression curing and/or whitening. Such a device should provide for a short cure-time and an irradiation which is capable to penetrate deep into the material to be activated. Further, such a device should provide an accurate and easily maintained registration of an image sensing means with the projection of irradiation to provide sharp real time imagery of the teeth.

SUMMARY OF THE INVENTION

The noted shortcomings of today's imaging equipment, namely the outlined x-ray procedure for analysis of tooth decay and the like, as well as the lack of large area irradiation sufficient to cure light large areas or thick coatings of activated material is overcome by using the herein device, providing benign visible and in some cases, invisible, radiation.

When used for tooth imaging, the device accomplishes real time imagery of one or a plurality of selected teeth by transmitting light of the proper visible or invisible wavelength through the teeth and detecting the image on the other side by means of charge coupled devices (CCDs) which is registered with the tooth and the light transmission device. The device provides great specificity as to which and how many teeth may be imaged through the use one or a plurality of different CCDs which register with individual teeth. While the preferred embodiment of the device makes use of an array of visible light emitters for the tooth illumination, it should be noted that the apparatus could also be modified to make use of other emitters with different wavelengths of light. For example a distributed array of x-ray radiating sources using the CCD's designed for reception of the transmitted x-rays could be operationally placed in the array as receivers, and such is anticipated. This is because CCDs are known to be responsive to visible light as well as soft x-rays.

The device in use for real time imagery illumination at a designated wavelength is projected through one or a plurality of determined teeth in the mouth from one side of the designated teeth. On the opposite side, registered with the tooth or teeth to be imaged, is the CCD which receives the energy projected therethrough. The output of one or more of the CCDs receiving the light transmission from the other side of the teeth is then transmitted to a computing device capable of interpreting the image from one or a plurality of the CCD's. Then a visual image can be displayed on a computer monitor in real time as long as the irradiation sources are turned on, or the images may be digitized and stored for later viewing. Using light transmissions in the visual light spectrum, the health hazard to the patient is virtually eliminated. Further, the dentist or medical provider may choose the exact tooth or teeth desired for imaging and the CCD and light transmission device registered therewith will yield the image of the tooth desired in real time.

While presently no small x-ray projection devices (chip size) exist which can be switched on or off on demand it is conceivable that such devices will become available in time, since laser chips already operate down to the 300 nm range. Consequently the use of projection devices which will project x-rays instead of visible light which is received by CCD's sensitive to x-rays is anticipated. There are however tiny x-ray non-switchable sources available today in the form of very low dosage radioactive materials which could be used in the described invention herein. While some applications will require only visible irradiation sources to render the dentist with enough information, other applications will require higher energy irradiation sources which operate below 400 nm down to 1 Angstrom to be effective for penetration of bone structure.

A second preferred embodiment of the device herein disclosed and described would replace the CCDs for receiving light from the opposite side of the tooth, with light emitting devices at the proper designated spectrum to accomplish teeth whitening. The above-noted problems for curing and whitening procedures are overcome by moving a plurality of such irradiation sources as close as possible to the compound to be activated and in sufficient numbers to properly activate a large area. Currently, LED chips or diode laser chips (devices) are the preferred activation irradiation means rather than conventional LEDs and diode lasers, which are somewhat larger in size. The use of a plurality of these chips preferably in positions to register with teeth or the media to be irradiated is an important improvement over conventional devices since they can be placed in large numbers on the same area otherwise occupied by a single packaged LED or laser diode. The resulting device thereby provides a very high power density of the emitted light to one or both sides of the patient's teeth. Additionally, should only partial illumination of one or a plurality of the patient's teeth or mouth be desired, the individual LED's or other light projection means could be turned on only in a small area of the mouth using a means to switch the individual light projection means on and off. The small chips are also suitable for a conformal apparatus design, which is not possible with the larger packaged devices.

In a third preferred embodiment of the device herein disclosed, the number of light sources is further increased and their locations are extended to three planes such as to illuminate the dental arch from inside, outside and the bottom/top side. This embodiment is particularly well suited for curing of thick dental impression material used to make models of a patient's mouth. The same considerations for high LED density applies for this configuration as in the previous case, as does the ability to illuminate the entire mouth or individual portions of it by energizing all of the light projection devices or just some in a desired location.

Both the embodiments used for teeth whitening or for impression forming may have additional components interspersed in between the emitter devices. Such components would be heat sensors, which would be separately connected to the electronic driving circuit and would provide a feedback means monitor the device for temperature and to assure patient comfort at all times. In cases where dental material is being hardened, such a means for feedback would also provide the dentist or user a manner to ascertain that the material being hardened has reached the critical temperature desired. As noted, the emitting sources can be wired such as to operate them in parallel, sequentially or only in specific areas of the dental arch, as desired by the dentist.

Moreover, in a current preferred embodiment a means for pulsing the light emitting devices such as pulsing the low-voltage (typically in the 3 to 5 volt range) irradiation sources is used to obtain higher peak power levels, which will result in deeper activation/curing depth of the materials. The pulsing of the illumination sources must be done in such a way that the devices are driven to their maximum current capability, yet there is sufficient off time between the pulses as to allow proper cooling of the devices. In this way the average energy into a device will be the same as in a continuous mode (cw) at much lower current level, but the peak power and therefore the activation or curing depth in the material being cured is considerably increased.

It should be noted that in the preferred embodiment of this device the addition of pulsing of the irradiation means with a proper duty cycle is most important. It is well known that the curing process for most of these compounds is not instantaneous and the hardness of the material improves with time. It is also known that the curing quality will depend on the total energy (Joules) absorbed by the compound being cured.

Therefore it would follow that the total result of curing with different duty cycles or even with cw would be the same, as long as the total delivered energy over the curing cycle is the same. However, the curing depth depends critically on the peak power achieved by the irradiation source, resulting in the ability to cure thicker layers of compounds the higher the peak power of the source.

It is also necessary to make sure that the irradiation means used are driven by nearly equal current levels, for application which require parallel operation; otherwise the hardest driven devices would prematurely fail due to excess heat generated internally. Device equalization can be accomplished either by testing and pre-selecting similar devices, or by driving each device with an individual series resistor, which will act as an equalizer for the drive current.

An object of this invention is to provide a provision of a dental imaging and curing device that uses low voltage and is capable of operation in the mouth with great precision as to radiation location and amount.

Another object of this invention is to provide a dental imaging and curing device which will provide for a short cure-time of dental material in the mouth through deep penetration of that material.

A further object of this invention is the provision of a dental imaging and curing device that provides accurate real time imagery one or a plurality of teeth using easily maintained registration of an image sensing means with the means for projection of irradiation.

An additional object of this invention is provision of a dental imaging and curing device that will allow for the activation of curing or teeth whitening material throughout the mouth evenly and at shortened times.

Still another object of this invention is to provide a dental imaging device that will provide accurate real time imaging of one or a plurality of teeth using visible light.

A further object of this invention is to provide a device that will image one or a plurality of teeth or cure dental material with great specificity as to location in the mouth.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Details of the disclosed invention, and preferred embodiments thereof will be further understood upon reference to the drawings, wherein.

DETAILED DESCRIPTION OF THE PREFERRED EMBODIMENTS

Figure 1:
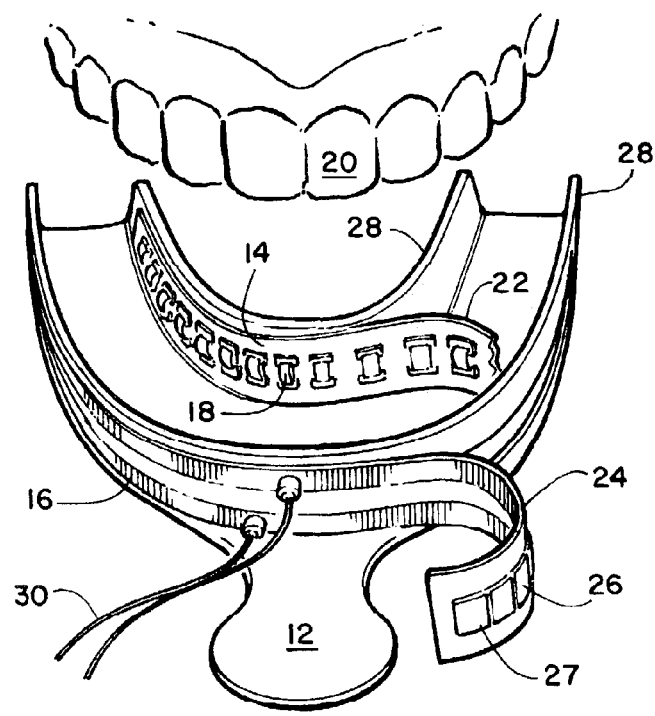
FIG. 1 is a perspective schematic drawing of a real-time imaging system for internal tooth structure, using visible light, or optionally x-rays.

Referring now to the drawings of the device 10, in FIGS. 1–5, FIG. 1 depicts a first preferred embodiment of the disclosed device 10 for dental imaging and irradiation of intra oral material, in the form of a real time teeth imaging apparatus, using visible illumination sources. The device in this preferred embodiment consists of four parts, a base plate 12 which serves as a support for the means for irradiation herein a means for light transmitting 14 at a desired frequency, an image receiving means 16 for receiving light transmissions for sensing and transmitting the image produced by the means for light transmitting communicating through a tooth or dental surface in the form of a means for receiving light transmissions structure 16 and the electronic circuits and means for provision of electrical power to the various electronic components.

A preferred illumination or transmitting sources in the form of Light Emitting Diode Chips which incorporate one or a plurality of light emitting diodes mounted on a circuit chip 34 here referred to as LEDs 18 other low power consuming means for light transmission, which are positioned to illuminate the teeth 20 from inside the arch of the teeth 20. In the current best mode the LED's 18 are mounted on a thin flexible circuit board 22, which holds a plurality of the LED 18 chips each of which may have one or plurality of light emitting diodes thereon and may also incorporate secondary optics and thereby provide the proper spatial radiation pattern for the desired light projection. The circuit board 22 provides a mount for the LED's 18 and the conventional electrical communication to them from the power source, and from them to a telemetry receiving and processing source, is formed such as to conform in shape to a dental arch and serves to illuminate the teeth from the inside. As depicted the LED's 18 or other light transmission means are shown on the inside arch transmitting to an imaging means for receiving the light transmissions which is on the outside of the arch. However this could be reversed and such is anticipated.

Living healthy teeth are normally translucent and sufficient light may be transmitted through the teeth to the outside so as to allow to form an image of the teeth using an electronic imaging means for receiving light transmission 16 which in the current best mode employ Charged Coupled Devices (CCD's). Typically, CCD IC circuit devices would be operatively arranged around the outside of the dental arch and operatively attached to a thin flexible circuit board 24. The circuit board 24 provides electrical communication to and from a plurality of charged couple devices, CCD's 26 thereby providing both power to run the CCD's 26 and a means to communicate images received by the CCD's from the light transmitted through the teeth 20 to a receiving device for reproduction and display of the images such as a computer and monitor. This provides electrical power to the CCDs 26 and enables the electronic readout of the pixel content of each CCD 26 by a communicating computing device with a visual display such as a monitor or liquid crystal display. Each CCD 26 in the current best mode contains a suitable micro-imaging lens 27 to form a high-resolution image of the illuminated particular section of the dental arch of the patient in which the device 10 is inserted and operated. Of course other image capturing devices could be used and such are anticipated, but the current best mode of the device 10 uses CCD's 26 with the lens 27 and IC control circuits. The IC circuits conventionally incorporated with such CCD's control their on or off condition and telemetry output to a remote receiving device.

The circuit boards 22 and 24 with the illuminating sources and the receiver devices (CCDs) operatively mounted for electronic communication and function thereon are mounted on sidewalls 28 on the baseplate 12 which provides a conduit for the required electronic communication through wires 30 or other means for electronic communication of data from the CCD's to the receiving communication device. Power is also communicated by wires 30 from a power source such as a battery 32 inside a handle 33 to provide the low voltage power source to operate the components of the device 10. Using a battery 32 allows operating the apparatus cordless, if so desired. Of course the handle 33 might also be substituted for a simple electrical interface that has the proper cooperative electrical fastener 46 to cooperatively and electrically engage a wire mount 48 on the base plate 12 to provide electrical power to the various components mounted on the device 10 and provide the telemetry from those components back to a communicating micro processing device or computer.

Communication of the CCD's with a computer or similar device capable of imaging the output of the CCD's 26 allows the user to scan sequentially the pixel content of the CCDs 26. The LED's 18 or other illumination devices best use a means for switching the devices on and off. This can be done with an electronic switch which is placed inline to interrupt the power provided to the LED's 18 when illumination by one or a plurality of such is or is not needed. Additionally, a switching means can be employed to interrupt the output of the CCDs to allow for a sequential reading of images from the individual CCD's 26 or they might all be switched on to give a real time image of all the teeth 20 together and adjacent to each other.

The output data stream from the CCD's 26 of the images captured thereon from the light transmitted at the proper spectrum or frequency to pass through the teeth from the radiating LED's 18 is either transmitted by wire 30 (corded) or by Radio or Infrared or other means for wireless transmission of data to an interface with a computer with a monitor or other image display device. This results in a real time display of the sectional images captured by the various CCDs 26 of the dental arch of a patient. Cracks, flaws, voids, fillings and cavities all give a different type of shadow images in the CCD captured teeth images, which the dental professional with some training will be able to recognize and distinguish from each other. This use of visible light also gives real time imaging without the need to use X-rays.

The computer using software written for the task would control and communicate the correct illumination sequence of the LED's 18 and the scanning of the CCDs 26, such that proper images can be displayed in real time on the computer monitor, or printed or stored in digital format for future reference and display.

In this embodiment it is preferable to use LED's 18 which project green or white light, as a means for illumination in order to get most detailed images of the internal tooth structure. A good example of such devices is Nichia's NSSG440 or NSSW440. These devices are available with different micro-lenses and come in various sizes as small as 1×0.5 mm for the APH1005PBC from Kingbright, or as large as 2×3.8 mm for the NSSX440/450 from Nichia. These small LED devices can be placed in large numbers and are operated with highest possible current densities. Sequential illumination of the LED 18 or similar illumination devices is preferred to achieve higher output power without device burn-out. This will result in brighter shadow images on the CCD 26 on the receiver side of the teeth 20.

The receiving means in the current best mode uses a number of micro CCDs 26 that have typically 768×494 pixels and have a sensing area of approximately 4.8×3.6 mm. Such CCDs 26 and the required driver electronics are available from a number of manufacturers such as Kodak, Sony, Panasonic, Sentech etc. To minimize the imaging distance required for this application special imaging micro lenses are used to provide the proper depth of field for a sharp image on the CCD's 26. The simplest lens may be just a pinhole. Switching of the various LED's 18 and CCD's 26 for sequential illumination and readout or continual illumination or combinations thereof may be provided by conventional miniature electronic switches identified by the location and type of device and located in line with power and output circuits of each such device and are operated by a controller or by the computer connected to the device 10, or each could be wired separately and controller operation of each CCD 26 and LED 18 could be provided by interrupting the individual circuit.

While this embodiment of the imaging apparatus is explicitly operated with benign visible light sources, it should be understood that the CCDs 26 are also receptive to x-rays and other light spectrums that are not visible. Consequently the device 10 could be used in such a mode provided suitable distributed, small x-ray or non visible illumination sources can be obtained and put in place of the presently used LED's 18. While such an embodiment using x-rays would still require x-ray irradiation sources, it would have the advantage to considerably lower the required dosage from today's necessary dosage because this embodiment brings the x-ray source as close as possible to the object (tooth) to be imaged. Such an apparatus would result in much improved patient safety during x-ray exposure and real time viable images of the teeth 20 being illuminated. In such an application with soft x-rays the described apparatus would be modified by replacing the LED chips with x-ray illumination means, or by removing the irradiating LED's 18 in FIG. 1. and adding a small, single x-ray source at the center of the arch, which could be activated by a switch means for the proper exposure time of short duration to illuminate the CCD's and capture the image of one or a plurality of teeth 20.

Figure 2:
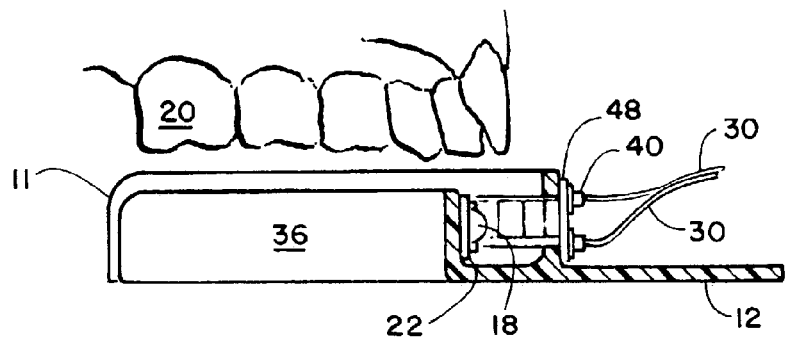
FIG. 2 is a side view of an embodiment of an apparatus for teeth whitening in accordance with this invention disclosure. Part of the attached electronic system is separately shown in FIG. 3.
Figure 3:
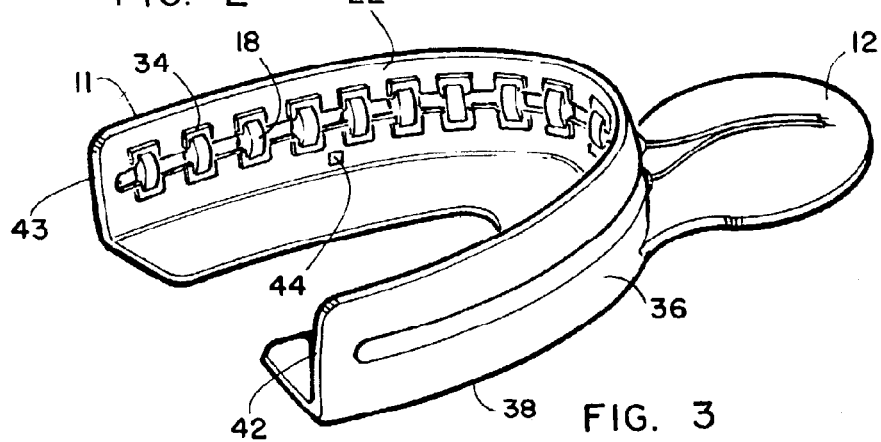
FIG. 3 is a detailed perspective view of the flexible circuit board used in the partial apparatus shown in FIG. 2.
Figure 4:
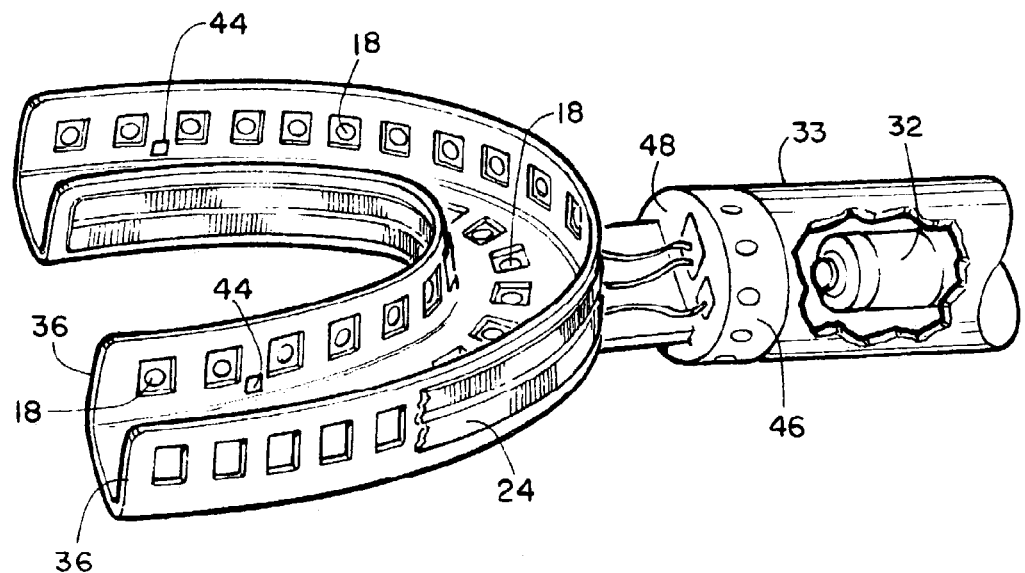
FIG. 4 is a schematic perspective view of a low power operated dental impression apparatus with curing sources on three surfaces.

FIGS. 2–4 are showing details of another preferred embodiment of the device 10 using light transmitted for teeth whitening. This embodiment is a somewhat less complex embodiment of the device 10 since it does not require any electronic imaging means for receiving and communicating light transmission yet still yields great improvement over current products used to activate whitening agents applied to the teeth 20.

The teeth whitening embodiment 11 of the device 10 consists of the base plate 12, a means to provide the device electrical power such as a battery, or other power pack, a controller and a flexible circuit board assembly 22 for the operative mounting and powering of the means for irradiation or illumination which can be shaped to conform to any dental arch. The means for illumination in this embodiment would be the same or similar to the LED's 18 as in the first embodiment but in the best embodiment would be in the blue spectrum such as an NSSB440from Nichia or similar devices. The LED's 18 are soldered to a thin printed or other circuit board 22 (PCB), which is thin and flexible such that it can be easily deformed. The devices used are pre-selected according to their current consumption, such that any consumption differences between devices are very small. This allows connecting all devices in parallel, without having to use individual series resistors for each device. The PCB is typically about 0.005" thick and has the desired number of receivers for the LED's 18 etched, mounted, or otherwise formed onto the surface to accommodate the devices, which is best shown in FIG. 3. The circuit board 22 is then molded together or otherwise fused into operative engagement with a flexible silicon or similar inert dental material used in a support structure 36, which has the LED's 18 or other irradiation devices properly situated and apertured to allow the irradiation to reach the desired targets on the teeth 20 when placed adjacent thereto. These surfaces on the teeth 20 during the whitening process are covered with oxidation material or other whitening compounds which act faster and in a better fashion when activated by a catalyst. The catalyst for the whitening material in this case is activation by one or a plurality of the LED's 18 or other irradiation or illumination means that provides the proper wavelength of emitted light in the proper positions to activate the whitening material completely and evenly. This in turn causes oxidation/whitening of the surfaces of the adjacently situated teeth 20.

Alternatively the flexible support structure 36 can be configured without apertures for the irradiation of the devices, provided the support material is sufficiently transparent for the irradiation wavelength of the LED's 18 or other irradiation means used to transmit through the support structure 36 material to activate the whitening compound. This would place the LED's 18 in a protected mounting internal to the body of the support structure 36 and avoid contact with the whitening substance and the fluids of the mouth.

The flexible support structure is attached to the base plate 12 in the current best mode only at a middle section 38, allowing the two wings 43 and 42, (left and right respectively) to be flexed to conformed to the arch of teeth 20 of the individual user. As human mouths are infinitely variable in the arch shape of their teeth 20, the device too is infinitely variable by flexing to fit individual mouths. This is shown in the schematic cross-section of FIG. 2. The flexible support structure 36 has also two wires 30 leading form the middle of the circuit board 22 to two contacts 40 operatively positioned on the base plate 12. An electronic power means for powering the irradiation devices such as a battery, or power pack or slow discharge capacitor, or other such means, would be communicated to the irradiation devices which are here shown as LED's 18 can be attached to these two contacts 40 by a snap-on or other conventional electrical connection fitting to power the devices on the circuit board 22. Cordless operation of the whitening embodiment 11 with a power pack unit is one preferred form of operation since allows a more mobile use. There is an optional way to operate the apparatus with a remote power pack unit by using a two-wire cable, which plugs into the base plate and connects to the remote power source such as a power supply or power pack.

The electronic part of the attached power pack unit consists of several components. First, a suitable means to provide electrical power such as a power pack or in the best embodiment a low voltage (7 to 8 Volts) battery such as a Nickel-Metal-Hydride, or Lithium-Ion battery 32 of sufficient capacity to drive the device array for 10 to 20 minutes is provided. The output of the battery is communicated to the LED's 18 or other irradiation means used through a switching means which in the current best mode would be a micro-processor controlled circuit (for example a Motorola MC 68HC series). The switching means in the current best mode features an asymmetric multi-vibrator (LM 555), which controls a switch (relay: V23026 series from Potter and Brumfield, or a solid state switch: MAX 4626 from Maxim), which can handle up to one ampere of electrical current. The switch may be controlled by a micro-processor or the like, to deliver a repetitive pulse sequence with a duty cycle of each LED 18 or other projecting irradiation means used for illumination which is adequate for the device array not to be excessively heated, but allowing maximum current drive and resulting illumination of the irradiation means during the pulse-on duration. Power from the electrical energy source fed to the device 11 is best fed to the LED's 18 or other used irradiation means, through a voltage regulator, which substantially eliminates any voltage variations of the electrical supply from the battery as it discharges during a teeth whitening procedure.

The control circuit may have other optional features such as duty cycle control of the duration of the on cycle and off cycle of the LED's 18 or other irradiation means by means of a software controlled micro-processor, which can monitor temperature or output power information from one or a plurality of monitoring devices 44 placed along the array. The monitoring devices 44 can be a temperature monitor which can monitor temperature, to assure patient comfort at all times. Monitoring temperature when using dental impression material would also provide a means to trigger an alarm to inform the dentist that the dental impression material has reached a predetermined temperature indicating completion of the impression. The monitoring devices 44 might also monitor tooth surface whiteness during a whitening procedure to provide an alarm means to the user that the whitening process being conducted is finished. These sensors can be small devices including one or a combination of such devices from a group consisting of an LED, CCD, Camera on a Chip, and electronic thermometer. The chosen means for monitoring using the chosen devices would be connected to a separate pair of wires, or multiplexed on the same wires used for the LED's or by separate wireless communication channel for the required feedback purpose. Experiments in reducing the current device to practice have shown that chips such as the NSSX series can serve equally well as a receiver/detector of light such as a CCD 26 when used passively (no power connected to the chip).

Such a reverse use of a chip, which is normally used as an irradiation transmitting means but serves now as a receiver, is extremely convenient for feedback purposes of temperature or power information of neighboring devices. It has been experimentally observed that such chips used as receivers are also wavelength selective. That means that a blue chip LED 18 such as the aforementioned NSSB440 will only respond to blue radiation and will automatically act as a filter and detect as a single device. This filter action is most effective for the longer wavelength side of the spectrum, meaning that the blue chip cuts off rather sharply towards green and red radiation but is still responsive to the UV side of the spectrum. Such a chip can be conveniently used for light meter purposes, as well as in the above described apparatus.

Furthermore, the micro-controller may have other functions such as recording/transmitting patient identification data and information regarding treatment parameters such as current, power, and temperature or the like. This information may be electronically communicated to a nearby computerized base station for live monitoring of the treatment procedure, as well as for storing case history.

FIG. 4 is a schematic perspective drawing of another preferred embodiment of the above described apparatus, which is configured with the same components but in a manner best used curing dental impressions. It is similar to the teeth whitening embodiment but has two support structures 36 essentially forming a pair of sidewalls surrounding the teeth 20 in the dental arch, instead of a single flexible PC support assembly. In this manner, the dental impression material, which will cover the teeth 20 can be irradiated from both sides, inside and outside. Furthermore, the base plate 12 which is used to attach both conforming flexible assemblies in the best mode of this embodiment would also have a plurality of irradiation sources such as the aforementioned LED's 18 imbedded in its structure such as to enable the curing of both sides and the underside of the impression material concurrently. This embodiment would speed up the process of hardening the dental impression material by the provision of curing light from three sides.

Figure 5:
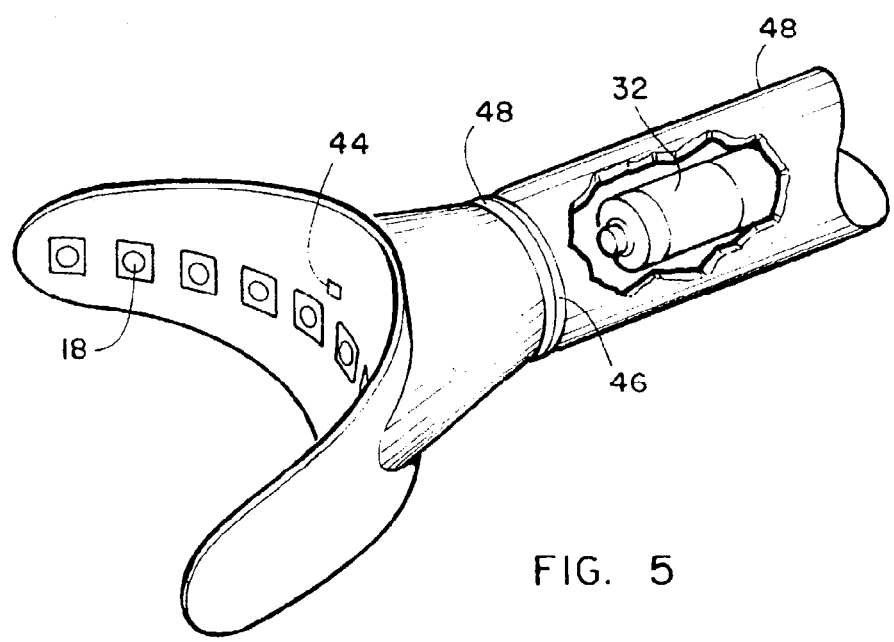
FIG. 5 is a perspective view of a low power hand held embodiment of the device for use in teeth whitening.

FIG. 5 depicts a perspective view of a low power hand held embodiment of the device for use primarily in teeth whitening. In this embodiment, a plurality of LED's 18 would be placed for proper registered illumination of the surfaces of teeth being whitened. This embodiment being hand held would have a handle which would double as a housing for batteries 32 to power the device. This embodiment also may employ the sensor 44 to monitor the whiteness of the teeth being treated and inform the user that the process is complete. This embodiment in the best mode would employ a battery and/or electronic circuit pack which can be removed for cleaning and charging. The electronic communication, pulsing of the LED's, and other aforementioned considerations and functions for this embodiment of the disclosed device are the same as the aforementioned embodiment for use in teeth whitening as previously discussed.

In conclusion it should be noted that all four preferred embodiments of the device herein disclosed, in the current best mode, are to be configured such that the battery and circuit packs can be removed, allowing the base plate and its flexible support structures to be auto-cleaved for sterility. This would also allow the same battery power pack or other electrical power means and controller means and computer means to be used with a plurality of differently configured devices from a kit of such devices. In this manner the same controller and power means could be used to power and control the imaging embodiment, or the teeth whitening embodiment, or the dental material hardening embodiment. Further, a plurality of each such embodiments could be provided in kit form with a plurality of different sized individual devices of each embodiment to allow the user to adjust easily between uses on adults and children or large and small mouths by simply picking the size of the individual embodiment, which best fits the mouth for the intended insertion for the intended of the three different procedures. In addition there may be a need to use a protective disposable sheath, which is transparent at the used irradiation source wavelength, but covers the entire apparatus inserted into the patient's mouth.

While the present invention has been described herein with reference to particular embodiments thereof, a latitude of modifications, various changes and substitutions are intended in the foregoing disclosure and will be appreciated that in some instance some features of the invention will be employed without a corresponding use of other features without departing from the scope of the invention as set forth in the following claims.

What is claimed is:

1. An intra-oral dental irradiation apparatus comprising:
   an arch shaped base plate, said base plate connecting a first sidewall to an opposing second sidewall;
   said first sidewall having an interior surface facing an inner surface of said second sidewall;
   an arched shaped cavity, said cavity defined by the substantially U-shaped area between said base plate, said interior surface and said inner surface;
   means to irradiate teeth occupying said cavity from multiple individual points of irradiation, said means to irradiate teeth powered by an electric current;
   means to pulse said means to irradiate teeth occupying said cavity wherein irradiation emitted therefrom is switched continuously between an energized state and a de-energized state;
   said means to irradiate teeth in said energized state producing said irradiation by employing a maximum of said electrical current communicated to said means to irradiate teeth to thereby provide maximum irradiation emission; and
   said means to irradiate teeth in said de-energized state ceasing said irradiation emission for sufficient time periods to allow cooling of said cavity to a determined temperature.

2. The intra-oral dental irradiation apparatus of claim 1 further comprising:
   said multiple individual points of irradiation located on at least one of said inner surface and said interior surface thereby irradiating one side surface of said teeth occupying said cavity.

3. The intra-oral dental irradiation apparatus of claim 2 further comprising:
   feedback means to monitor the cavity temperature in said cavity and adjust said time periods of said de-energized state to durations which maintain said cavity temperature at a specified temperature level.

4. The intra-oral dental irradiation apparatus of claim 3 further comprising:
   feedback means to monitor the whiteness of said teeth occupying said cavity and communicate an alarm when said whiteness reaches a specified whiteness level.

5. The intra-oral dental irradiation apparatus of claim 2 further comprising:
   feedback means to monitor the whiteness of said teeth occupying said cavity and communicate an alarm when said whiteness reaches a specified whiteness level.

6. The intra-oral dental irradiation apparatus of claim 2 further comprising:
   light emitted by said multiple points of irradiation being of a spectrum act as a catalyst to harden dental impression material.

7. The intra-oral dental irradiation apparatus of claim 2 further comprising:

light emitted by said multiple points of irradiation being of a spectrum act as a catalyst to activate tooth enamel whitening material deposited on said teeth.

8. The intra-oral dental irradiation apparatus of claim 7 further comprising:
feedback means to monitor the whiteness of said teeth occupying said cavity and communicate an alarm when said whiteness reaches a specified level.

9. The intra-oral dental irradiation apparatus of claim 1 further comprising:
said multiple individual points of irradiation located on both said inner surface and on said interior surface thereby irradiating both sides of said teeth occupying said cavity.

10. The intra-oral dental irradiation apparatus of claim 9 further comprising:
said multiple individual points of irradiation additionally located on said base plate thereby irradiating said teeth occupying said cavity from three different sides.

11. The intra-oral dental irradiation apparatus of claim 10 further comprising:
feedback means to monitor the cavity temperature in said cavity and adjust said time periods of said de-energized state to durations which maintain said cavity temperature at a specified temperature level.

12. The intra-oral dental irradiation apparatus of claim 11 further comprising:
feedback means to monitor the whiteness of said teeth occupying said cavity and communicate an alarm when said whiteness reaches a specified whiteness level.

13. The intra-oral dental irradiation apparatus of claim 10 further comprising:
light emitted by said multiple points of irradiation being of a spectrum act as a catalyst to harden dental impression material.

14. The intra-oral dental irradiation apparatus of claim 10 further comprising:
light emitted by said multiple points of irradiation being of a spectrum act as a catalyst to activate tooth enamel whitening material deposited on said teeth.

15. The intra-oral dental irradiation apparatus of claim 14 further comprising:
feedback means to monitor the whiteness of said teeth occupying said cavity and communicate an alarm when said whiteness reaches a specified level.

16. The intra-oral dental irradiation apparatus of claim 9 further comprising:
feedback means to monitor the cavity temperature in said cavity and adjust said time periods of said de-energized state to durations which maintain said cavity temperature at a specified temperature level.

17. The intra-oral dental irradiation apparatus of claim 16 further comprising:
feedback means to monitor the whiteness of said teeth occupying said cavity and communicate an alarm when said whiteness reaches a specified whiteness level.

18. The intra-oral dental irradiation apparatus of claim 9 further comprising:
light emitted by said multiple points of irradiation being of a spectrum act as a catalyst to harden dental impression material.

19. The intra-oral dental irradiation apparatus of claim 9 further comprising:
light emitted by said multiple points of irradiation being of a spectrum act as a catalyst to activate tooth enamel whitening material deposited on said teeth.

20. The intra-oral dental irradiation apparatus of claim 19 further comprising:
feedback means to monitor the whiteness of said teeth occupying said cavity and communicate an alarm when said whiteness reaches a specified level.

21. The intra-oral dental irradiation apparatus of claim 1 further comprising:
feedback means to monitor the cavity temperature in said cavity and adjust said time periods of said de-energized state to durations which maintain said cavity temperature at a specified temperature level.

22. The intra-oral dental irradiation apparatus of claim 1 further comprising:
light emitted by said multiple points of irradiation being of a spectrum act as a catalyst to harden dental impression material.

23. The intra-oral dental irradiation apparatus of claim 1 further comprising:
light emitted by said multiple points of irradiation being of a spectrum act as a catalyst to activate tooth enamel whitening material deposited on said teeth.

24. The intra-oral dental irradiation apparatus of claim 23 further comprising:
feedback means to monitor the whiteness of said teeth occupying said cavity and communicate an alarm when said whiteness reaches a specified level.

25. An intra-oral dental irradiation apparatus comprising:
a base plate, said base plate connecting a first sidewall to an opposing second sidewall;
said first sidewall having an interior surface facing an inner surface of said second sidewall;
an arched shaped cavity, said cavity defined by the substantially U-shaped area between said base plate, said interior surface and said inner surface;
means to irradiate teeth occupying said cavity from multiple individual points of irradiation;
said multiple individual points of irradiation located on at least one of said first sidewall and said second sidewall thereby transmitting irradiation through said teeth occupying said cavity;
means to receive irradiation emitted from said multiple individual points of irradiation and transmitted through said teeth, and produce an electronic image of one or a plurality of said teeth located in said cavity; and
means to communicate said electronic image to a remote display device wherein said electronic image may be viewed or reproduced.

26. The intra-oral dental irradiation apparatus of claim 25 further comprising:
said means to irradiate teeth occupying said cavity from multiple individual points of irradiation comprise a plurality of light emitting diode devices; and
said means to receive irradiation emitted from said multiple individual points of irradiation and produce an electronic image of one or a plurality of said teeth located in said cavity comprise one or a plurality of charged coupled devices, wherein said irradiation emitted from said light emitting diode devices and transmitted through said teeth is received by said charged coupled devices and communicated electronically to a computer imaging device which thereafter produces said image.

27. The intra-oral dental irradiation apparatus of claim 26 further comprising:

switching means to individually control each of said means to produce and electronic image, said switching means allowing each said means to produce and electronic image to be switched from a receiving state wherein said image is communicated to said computer imaging device, to a dormant state, wherein no image is communicated, thereby providing a means for selective image production of one or more of said teeth.

* * * * *